United States Patent
Chang et al.

(10) Patent No.: US 10,046,088 B2
(45) Date of Patent: *Aug. 14, 2018

(54) NANOSCALE COLLAGEN PARTICLES AND MEMBRANES

(71) Applicant: EMPIRE TECHNOLOGY DEVELOPMENT LLC, Wilmington, DE (US)

(72) Inventors: Hengky Chang, Singapore (SG); Henry Leung, Singapore (SG)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 609 days.

This patent is subject to a terminal disclaimer.

(21) Appl. No.: 14/606,672

(22) Filed: Jan. 27, 2015

(65) Prior Publication Data
US 2015/0140064 A1    May 21, 2015

Related U.S. Application Data

(63) Continuation of application No. 12/992,120, filed as application No. PCT/SG2010/000179 on May 7, 2010, now Pat. No. 8,951,598.

(51) Int. Cl.
*C08L 89/06* (2006.01)
*A61L 27/40* (2006.01)
(Continued)

(52) U.S. Cl.
CPC .......... *A61L 27/26* (2013.01); *A61L 15/225* (2013.01); *A61L 15/325* (2013.01); *A61L 15/40* (2013.01);
(Continued)

(58) Field of Classification Search
CPC .......... A61L 26/0028; A61L 23/0033; A61L 26/0052; A61L 27/3821; A61L 2400/12; A61L 27/40; C08L 89/06
(Continued)

(56) References Cited

U.S. PATENT DOCUMENTS

| 4,948,540 A | 8/1990 | Nigam |
| 4,950,699 A * | 8/1990 | Holman ............... A61L 15/585 424/116 |

(Continued)

FOREIGN PATENT DOCUMENTS

| EP | 0 914 826 | 5/1999 |
| JP | 2005-206567 | 8/2005 |

(Continued)

OTHER PUBLICATIONS

Chen et al. Asymmetric Chitosan Membrane Containing Collagen I Nanospheres for Skin Tissue Engineering. Biomacromolecules 2009, 10, 1642-1649.*

(Continued)

*Primary Examiner* — Cachet I Sellman (57) ABSTRACT

Nano scale collagen particles can be obtained from an embrittling and attrition process that reduces the size of collagen particles to the nano scale. These nano scale collagen particles have many favorable properties such as providing beneficial and enhanced properties for cell seeding and wound healing. The nano scale collagen particles can be included in biocompatible (e.g., biostable or biodegradable) compositions and are useful for wound treatment and management, as well as in cell cultures and tissue engineering implants.

26 Claims, 7 Drawing Sheets

(51) Int. Cl.
| | |
|---|---|
| A61L 27/26 | (2006.01) |
| A61L 15/32 | (2006.01) |
| A61L 15/40 | (2006.01) |
| A61L 15/44 | (2006.01) |
| A61L 15/46 | (2006.01) |
| A61L 27/24 | (2006.01) |
| A61L 27/38 | (2006.01) |
| A61L 27/48 | (2006.01) |
| A61L 27/54 | (2006.01) |
| C07K 14/78 | (2006.01) |
| A61L 15/22 | (2006.01) |
| A61L 15/42 | (2006.01) |
| A61L 27/50 | (2006.01) |

(52) U.S. Cl.
CPC ............... *A61L 15/42* (2013.01); *A61L 15/44* (2013.01); *A61L 15/46* (2013.01); *A61L 27/24* (2013.01); *A61L 27/3813* (2013.01); *A61L 27/3839* (2013.01); *A61L 27/3895* (2013.01); *A61L 27/48* (2013.01); *A61L 27/50* (2013.01); *A61L 27/54* (2013.01); *C07K 14/78* (2013.01); *A61L 2400/12* (2013.01); *A61L 2430/02* (2013.01); *A61L 2430/34* (2013.01)

(58) Field of Classification Search
USPC .......................................... 427/2.1, 2.31, 240
See application file for complete search history.

(56) References Cited

U.S. PATENT DOCUMENTS

| | | | | |
|---|---|---|---|---|
| 5,196,185 | A * | 3/1993 | Silver | A61K 9/7015 424/428 |
| 5,837,278 | A | 11/1998 | Geistlich et al. | |
| 6,046,160 | A | 4/2000 | Obi-Tabot | |
| 6,585,997 | B2 * | 7/2003 | Moro | A61K 9/006 424/434 |
| 6,660,829 | B1 | 12/2003 | Maffia | |
| 6,887,488 | B2 | 5/2005 | Cui et al. | |
| 2003/0032601 | A1 * | 2/2003 | Kreuter | A23J 1/04 424/40 |
| 2007/0016123 | A1 * | 1/2007 | Jensen | A61F 13/0203 602/57 |

FOREIGN PATENT DOCUMENTS

| | | | |
|---|---|---|---|
| JP | 2006-016381 | | 1/2006 |
| JP | 2006013681 | | 1/2006 |
| JP | 2006013681 | A * | 1/2006 |
| JP | 2006016381 | A | 1/2006 |
| WO | 90/00060 | | 1/1990 |
| WO | 03/099230 | | 12/2003 |

OTHER PUBLICATIONS

Chen et al. Influence of Collagen I Nanospheres on the Growth and Osteogenic Difference of Rat Bone Marrow Stromal Cells. Journal of Medical and Biological Engineering, 2009. 29(6): 284-289.*

Park, J. K., "A composite scaffold composed of collagen nano-fiber on amniotic membrane for bioartificial periodontal ligament" Theories and Applications of Chem. Eng., 2007, vol. 13, No. 1 pp. 339.
Martina Nicklas, et al "Preparation and characterization of marine sponge collagen nanoparticles and employment for the transdermal delivery of 17β-estradiol-hemihydrate" Drug Development and Industrial Pharmacy, 2009; 35(9): 1035-1042.
Chi H. Lee, et al "Biomedical applications of collagen" International Journal of Pharmaceutics 221 (2001) 1-22.
S.J. Chang, et al "Preparation of nano-sized particles from collagen II by a high-voltage electrostatic field system" IEEE Proc.-Nanobiotechnol., vol. 153, No. 1, Feb. 2006.
Markus J. Buehler "Nature designs tough collagen: Explaining the nanostructure of collagen fibrils" PNAS, Aug. 15, 2006, Wol. 103, No. 33, pp. 12285-12290.
Hassan Niknejad, et al "Properties of the amniotic membrane for potential use in tissue engineering" European Cells and Materials vol. 15 2008 pp. 88-99.
Zuolin Cui, et al "Structures and properties of nano-particles prpared by hydrogen arc plasma method" Thin Solid Films 318 (1998) 76-82.
Xiaoxia Chen, et al "Preparation of cyclosporine A nanoparticles by evaporative precipitation into aqueous solution" International Journal of Phamaseutics 242 (2002) 3-14.
Bobby G. Sumpter, et al "Recent developments in the formation, characterization, and simulation of micron and nano-scale droplets of amorphous polymer blends and semi-crystalline polymers" Polymer 44 (2003) 4389-4403.
Richard J. Malcolmson, et al, "Dry powder formulations for pulmonary delivery" PSTT vol. 1, No. 9 Dec. 1998.
H. Yoshimoto, et al "A biodegradable nanofiber scaffold by electrospinning and its potential for bone tissue engineering" Biomaterials 24 (2003) 2077-2082.
Y.K. Luu, et al "Development of a nanostructured DNA delivery scaffold via electrospinning of PLGA and PLA-PEG block copolymers" Journal of Controlled Release 89 (2003) 341-353.
Mingru Zhou, et al "Particle size and pore struture characterization of silver nanoparticles prepared by confined arc plasma" Journal of Nanomaterials, vol. 2009, Article ID 968058, 2009.
Shyh Ming Kuo, et al "Preparation of nano-sized particles of collagen II by an electrostatic field system" Proceedings of the 2005 IEEE Engineering in Medicine and Biology 27th Annual Conference, Shanghai, China, Sep. 1-4, 2005.
Shyh Ming Kuo, et al "Preparation of nano-sized collagen I and collagen II particles" Bioinformatics and Biomedical Engineering, 2008. ICBBE 2008, The 2nd International Conference on Publication Date: May 16-18, 2008, On pp. 1417-1419 Digital Object Identifier: 10.1109/ICBBE.2008.683.
Ryan H. Fitzgerald, et al "Collagen in wound healing: are we onto something new or just repeating the past?" The Foot and Ankle Online Journal, 2009 [Online: http://faoj.wordpress.com/2009/09/01/collagen-in-wound-healing-are-we-ont-something-new-or-just-repeating-the-past/].
Hannele Eerikaeinen, et al "Preparation of polymeric nanoparticles containing corticosteroid by a novel aerosol flow reactor method" International Journal of Pharmaceutics 263 (2003) 69-83.
International Search Report and Written Opinion for International Application No. PCT/SG2010/000179 dated Jul. 22, 2010.

* cited by examiner

NANOSCALE COLLAGEN PARTICLES AND MEMBRANES

CROSS-REFERENCE TO RELATED APPLICATIONS

The present application is a continuation application under 35 U.S.C. § 120 of U.S. patent application Ser. No. 12/992,120, filed on Nov. 11, 2010, now U.S. Pat. No. 8,951,598, which in turn is a U.S. National Stage filing under 35 U.S.C. § 371 of International Application No. PCT/SG10/00179, filed on May 7, 2010.

BACKGROUND

Collagen is a protein that forms the major part of extracellular matrixes. Under normal physiological conditions, collagen can undergo a spontaneous self-assembly reaction and then form fibrous structures. This self assembly reaction is an entropy-driven process and is influenced by the effective charges on the collagen molecules, which is termed fibrillogenesis. Collagen has various advantages as a biomaterial, such as excellent biocompatibility and weak antigenicity, and is widely used as a carrier system for the delivery of drugs, proteins and genes. So far, the collagen matrixes prepared have usually been limited to the fibrillar structural forms. Collagen-based micro-particles have demonstrated their usefulness as a sustained release medium for antimicrobial agents or as a parental carrier for cytotoxic reagents or gene delivery.

Nanoparticles show unique physical and chemical properties that are different from those of the conventional materials due to their ultra-fine size and being at a subcellular level. Nanoparticles can have increased surface area, high adsorptive capacity, and other properties associated with smaller particles, such as smaller size and mass. The nano scale size range can provide a dimension that is conducive to physico-physiological phenomena and functions at a biologically compatible level.

Various chemical or physical processing techniques have been developed to manufacture nano scale particles. Among these techniques, solvent-based processes, such as emulsification-solvent evaporation, emulsification-solvent diffusion and precipitation methods, are often used to manufacture nano scale particles. Dry and wet milling processes are also widely used to reduce the particle size for the preparation of nano scale particles.

SUMMARY

Generally, improved nano scale collagen particles can now be obtained from an embrittling and attrition process that reduces the size of collagen particles to the nano scale. These nano scale collagen particles have many favorable properties such as, but not limited to, one or more of providing beneficial and enhanced properties for cell seeding and wound healing. The nano scale collagen particles can be included in biocompatible (e.g., biodegradable or biostable) compositions, some of which can be useful for wound treatment and management among others.

According to an aspect, a method for manufacturing nano scale collagen particles can include: embrittling a composition of collagen particles; and reducing the size of the collagen particles to have a nano scale dimension. The embrittling process can include reducing a temperature of the collagen particles to cause cryogenic embrittling. Also, the embrittling can include contacting the collagen particles with a cryogenic fluid or a placing the collagen particles in a thermally conducting container that is brought into contact with the cryogenic fluid. Prior to embrittling, the collagen particles can be provided that have a dimension greater than about 1 micron.

According to an aspect, the method can include drying the embrittled collagen particles. Such drying can be under vacuum. It can be advantageous to dry without heating the embrittled collagen. Various drying or moisture removing processes can be used before, during, or after embrittling. Moisture or water absorbing substances can be used to trap water, and such substances can be removed prior to reducing the size of the collagen. One example of drying would be freeze drying the collagen particles.

According to an aspect, the process of reducing the size of the collagen particles can include an attrition process, such as high energy attrition. High energy attrition can be performed by various techniques that reduce the size of the collagen particles to the nano scale. For example, the high energy attrition can include milling the collagen particles with one or more milling balls. The milling can be performed at high rotational speeds.

According to an aspect, the nano scale collagen particles can be included in a composition. As such, the composition can include one or more nano scale collagen particles incorporated into a biocompatible (e.g., biodegradable or biostable) material. The biodegradable material can include a biodegradable polymer. The nano scale collagen particles can be substantially uniformly distributed within the composition. This can produce a composition with a substantially homogeneous distribution of the nano scale particles.

In one embodiment, the composition having the biocompatible (e.g., biodegradable or biostable) material and the nano scale collagen particles can be formed into a thin Membrane. Such a membrane can include nano scale collagen particles having an average dimension of about 1 nm to 1 micron, or about 200 nm. Also, the thin membrane can have a thickness from about 10 microns to about 100 microns, or about 50 microns.

In one embodiment, a method for manufacturing an article can include preparing a composition having the biocompatible (e.g., biodegradable or biostable) material and nano scale collagen. The manufacturing can include: mixing nano scale collagen particles with a biocompatible material; and forming the article to include the nano scale collagen particles distributed in the biocompatible material.

According to an aspect, the article of manufacture can be a thin membrane that is prepared as a bandage. The bandage can be used for wound management and can be placed within a wound of a subject. The bandage with nano scale collagen particles can be useful for wound management because the collagen particles can be favorable for cell infiltration into the membrane and healing.

According to an aspect, a method for manufacturing a thin membrane can include mixing nano scale collagen particles with a biocompatible (e.g., biodegradable or biostable) material, and forming a thin membrane to include the nano scale collagen particles with the biocompatible material. The process of forming the membrane can include various types of methods of membrane formation, such as spin-coating the biocompatible material and nano scale collagen particles onto a substrate.

In one embodiment, a method for culturing cells can be performed with a cell culture article that is prepared from a composition having the biocompatible material containing the one or more collagen particles. Such a cell culture method can include introducing a cell culture article (e.g., cell culture insert) into a cell culture chamber. One or more cells can be cultured in the cell culture chamber such that the one or more cells migrate and/or proliferate on or within the cell culture article. For example, the cell culture article can be shaped as a cell culture insert.

In one embodiment, the composition having the biocompatible material containing the nano scale collagen particles can be prepared as a tissue implant article. For example, the biocompatible material can be shaped into a biocompatible tissue engineering scaffold and contain the one or more nano scale collagen particles. The tissue engineering scaffold can also include one or more cells such that the scaffold having the cells can be implanted as a tissue implant. As such, a tissue engineering scaffold can include one or more cells and be implanted into the body of a subject to provide the cells to the subject. The cells can form a tissue as desired.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

As used herein, a "nano scale" is meant to refer to a size that is larger than 1 nano meter and less than a micron, such as less than 999 nano meters when referring to size. The nano scale covers all ranges from 1 to 999 nano meters, which can include sizes ranging from 10s of nano meters to 100s of nano meters. Specific examples of particles in the nano scale are 100 nm and 200 nm.

As used herein, term "embrittling," "bristling," or other derivatives thereof is meant to refer to the process of causing a collagen composition to become more brittle, typically by reducing its temperature and/or reducing water content. The embrittling process can include exposing the collagen to an environment having a reduced temperature, which can include exposure to liquids or gases (e.g., air), sufficient for causing the collagen to become more brittle. The brittle status of a collagen composition or particle allows for the composition or particle to break (or to be broken) into fragments or pieces and reduce the size of the composition or particle.

As used herein, the term "attrition" is meant to refer to the reduction in size or breaking or fragmenting of collagen compositions or particles into smaller sizes. For example, attrition of a micron scale particle produces one or more smaller particles.

Novel nanotechnology processing methods can now be used to reduce collagen material to nano scale sizes (e.g., less than 1 micron, such as 999 nm or less). The nano scale collagen can behave differently with improved material properties over its bulk or micron scale (e.g., greater than 1 micron) counterpart. The collagen powder/particles in its bulk or micron scale are not able to be dissolved by normal water, but can be dissolvable under acidified water with HCl. However, such dissolution can be problematic when attempted for cellular absorption and can result in poor bioavailability. Now nano scale collagen prepared as described herein can have improved properties such as increased solubility and cell growth characteristics.

The nano scale collagen can be prepared by a new process that leads to nano scale collagen particles from micron scale collagen particles. The nano scale collagen can have improved biological properties. The method for producing the nano scale collagen can include cryogenic brittling and high energy attrition to break down the collagen particle to the nano scale size range.

The nano scale collagen can be beneficial in wound management. The nano scale collagen can be used as a wound dressing alone or with other substances or as particles, membranes, or bandages. This can include the nano scale collagen being formed into a thin layer membrane suitable for wound management. The membrane can include biocompatible (e.g., biodegradable or biostable) materials that form the membrane with the nano scale collagen dispersed therein. For example, the nano scale collagen particle can be mixed with a biodegradable/bioresorbable polymer matrix and spun to form a thin layer membrane with uniformly distributed nano scale collagen particle within the biodegradable polymer. Such a membrane is useful for wound healing treatment, among others.

The thin membrane having nano scale collagen can be used in homes, in hospitals, or in any other medical care environment to treat various types of wounds. Wounds are generally classified into two groups: involving the loss of skin tissue; or without significant loss of skin tissue (e.g., incised). Both of these types of wounds have different healing properties, and the thin membrane is useful for both types of wounds. In an incised wound where there is no loss of skin tissue, the wound healing centers on reproduction of connective tissue which is primary healing. As such, the thin membrane can be useful for primary healing. In contrast, for a wound that has a loss of skin tissue, there will be secondary healing which is regeneration of epidermis layer extending from the circumferential portions surrounding the injuries after the primary healing. The thin membrane can be useful for secondary healing due to the improved biological properties of the nano scale collagen. For example, the wounds treatable with the thin membrane can include loss of skin, open wounds, skin burns, surgical wounds, congelation, decubitus, or the like. The thin membrane can be useful in improving the healing rate of primary and secondary healing.

The thin membrane can be prepared into various sizes, such as those large enough to cover a large wound with skin tissue loss. The thin film can be a small size suitable for a cut, incision, or other primary healing wound as well as a large size that can be effective for secondary healing where a large amount of skin cell proliferation is needed. As such, the thin membrane can be useful for wounds ranging from small cuts to large wounds that would traditionally need a skin graft. The thin membrane can be a useful wound dressing material capable of removing exudate from a wound while providing protection for the wound. The thin membrane has several characteristics for improved wound healing including, but not limited to, one or more of: high porosity for gas permeation and a good barrier for protection of the wound from infection and dehydration.

The nano scale collagen particles can be prepared with a new process that can include embrittling collagen with cryogenic cooling, which can be with liquid nitrogen or other cryogenic fluid (e.g., cold liquids and gases). As used herein, "embrittling" is meant to refer to a process of increasing hardness with little tensile strength, such that it is easily broken apart and reduced in size. Also, the embrittling process can include lyophilizing or freeze drying the collagen to extract moisture components from the micron scale collagen so as to embrittle and dry the collagen micron particle. The embrittled collagen particles can then be reduced in size by attrition, such as by a high energy attrition machine.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The embrittling process can include embrittling a composition of collagen particles, and then reducing a size of the collagen particles to have a nano scale dimension. The embrittling can include reducing the temperature of the collagen particles to cause cryogenic embrittling. The collagen particles that are reduced in size can be provided with a dimension greater than about 1 micron prior to the embrittling process. The embrittling process can include contacting the collagen particles or a vessel containing the collagen particles with a cryogenic fluid or other medium that can reduce temperature. The embrittling process can also include removing some or all of the water from the collagen particles.

An example of embrittling can include freeze-drying the collagen particles. For example, the embrittling process can include: placing the composition of collagen particles into a vessel; contacting the vessel with a cryogenic fluid; and placing the vessel under vacuum to reduce pressure inside the vessel so as to sublime water from the collagen particles.

The embrittling process can include obtaining a collagen powder and subjecting the collagen to sufficiently low temperatures to embrittle the collagen. The low temperature can be obtained by using cryogenic liquid (e.g., liquid nitrogen or acetone/dry ice baths) in direct or indirect (e.g., collagen can be in a container that is submerged into cryogenic fluid) contact with the collagen for a sufficient duration to embrittle the collagen. For example, the sufficient duration can be at least 5 minutes, 10 minutes, 15 minutes or 30 minutes or longer.

Optionally, the embrittling can be followed by processing under vacuum so as to remove excess water by sublimation. Accordingly, the embrittling process can be similar to lyophilization or freeze drying. The vacuum processing can be performed for a duration of at least 12 hours, 24 hours, or 48 hours depending on the moisture content. However, the collagen can be thoroughly dried by heat or chemical water extraction prior to embrittling so that the vacuum processing of cold collagen can be optional.

The embrittling process can include reducing a temperature of the collagen particles to cause cryogenic embrittling. This can include reducing the temperature to less than 0 degrees C., less −25 degrees C., less than −50 degrees C., less than −75 degrees C., or even less than −100 degrees C. Also, the embrittling can include contacting the collagen particles with a cryogenic fluid. The cryogenic fluid can be liquefied gases such as helium, hydrogen, methane, nitrogen, oxygen, air, and fluorine, which can have low temperatures between −150. degrees F. to −450 degrees F. Cooling baths can also be used, such as those shown in Table 1.

TABLE 1

| Mixture | T (° C.) |
| --- | --- |
| CaCl2•6 H2O/ice 1:2.5 | −10 |
| NaCl/ice 1:3 | −20 |
| carbon tetrachloride/CO2 | −23 |
| acetonitrile/CO2 | −42 |
| CaCl2•6 H2O/ice 1:0.8 | −40 |
| Acetone/CO2 | −78 |
| Methanol/N2 | −98 |
| Liquid N2 | −196 |

Prior to embrittling, collagen particles can be provided that have a dimension greater than about 1 micron. The collagen can also be provided in various formats and configurations. The collagen can be from any source.

In one embodiment, the method can include drying the collagen. Such drying can be performed by various drying or moisture removing processes before, during, or after embrittling. Moisture or water absorbing substances can be used to trap water, and such substances can be removed prior to reducing the size of the collagen. Optionally, the collagen can be dried prior to embrittling by heat. Also, the drying can include drying under vacuum that can remove the water from the collagen.

The process of reducing the size of the collagen particles can include an attrition process, such as high energy attrition or impaction that causes micron scale collagen particles to break down into nano scale collagen particles. The size reduction process can be a high energy impaction milling/attrition process for a duration to obtain very fine collagen powders/particles in the nano scale range. High energy attrition can be performed by various techniques that reduce the size of the collagen particles to the nano scale. For example, the high energy attrition can include milling, chopping, cutting, grinding, or the like. A milling process can include milling balls of various sizes.

For example, the high energy milling process can include about 500 RPM rotational speed for 20 to 30 hours with one or more milling balls. The milling ball can be one or a mixture of different sized milling balls, such as for example 10 mm, 3 mm, and/or 2 mm diameter or any other suitable size depending on the scale. For small quantities millimeter scale balls can be used; however, large scale manufacturing can use milling and milling balls on the order of 5 cm, 10 cm, 20 cm, or larger. However, any size of mill ball can be used by modulating the milling speed or duration. Also, when multiple sized milling balls are used, they can be present at various weight ratios with more being large or more being small or being nearly equivalent at a ratio of 1:1:1 for each milling ball size. For each milling, the amount of freeze dried (e.g., embrittled) collagen to start can be about 1:5 weight ratio with milling balls; however, the ratio can range from 10:1 to 1:10, which includes 1:5 and 5:1 ratios.

Figure 1:
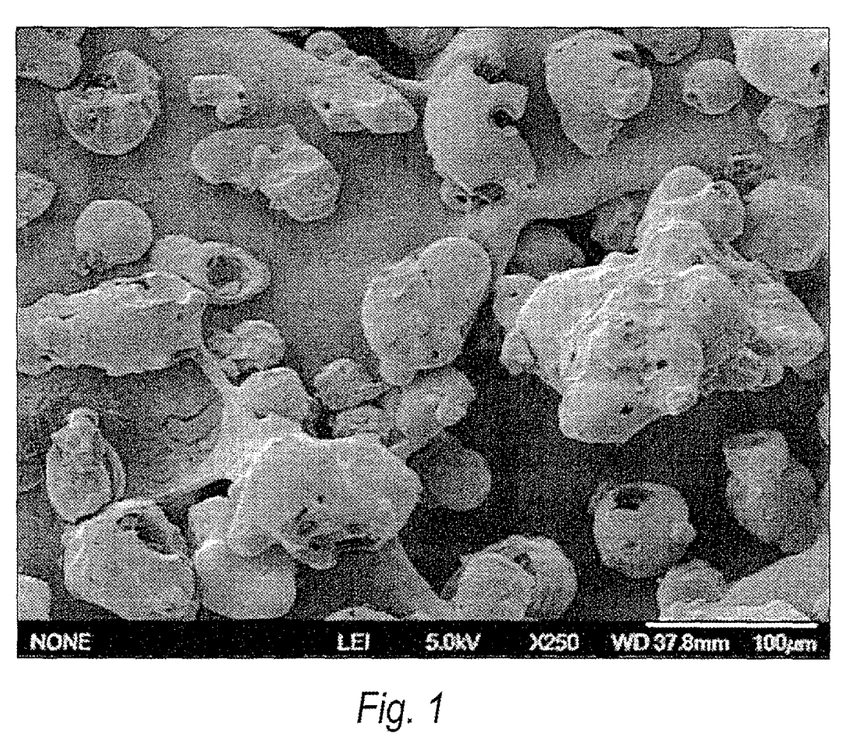
FIG. 1 is an example of an image of the original commercial micron sized collagen that was prepared into nano scale collagen particles.
Figure 2:
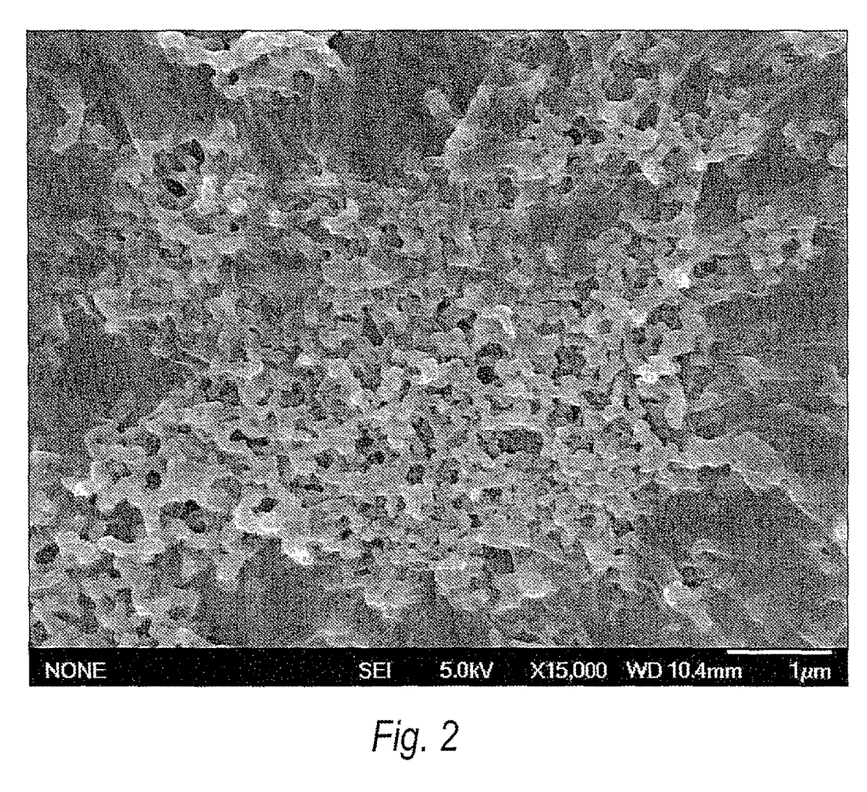
FIG. 2 is an example of an image of nano scale collagen having average size 200 nm, which was prepared from the collagen of FIG. 1.
Figure 3:
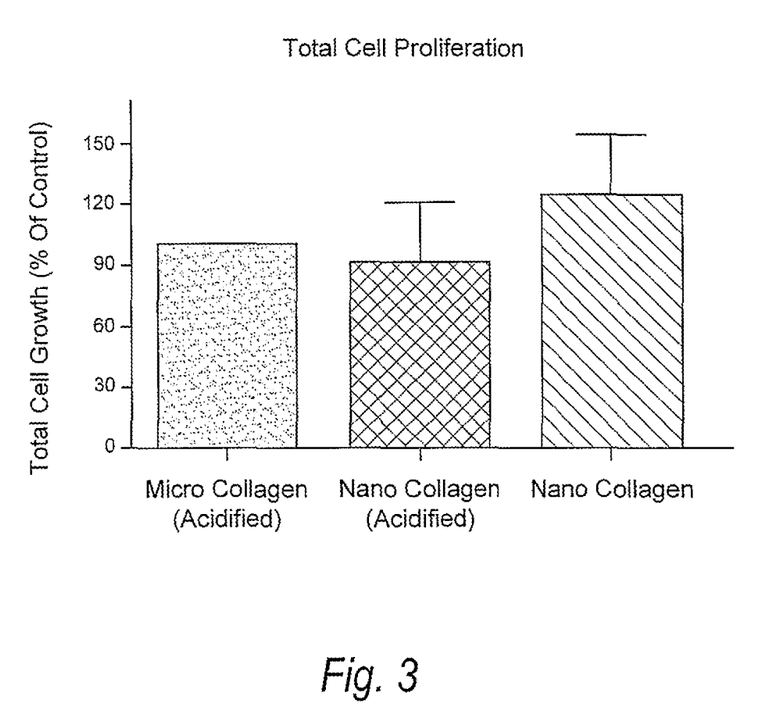
FIG. 3 is an example of a graph illustrating a comparison of total cell growth between micron scale collagen and nano scale collagen particles.

The embrittling and attrition process is able to produce nano scale collagen from micron scale collagen (see FIG. 1, which shows average size being around 50 microns with many particles being 100 microns or larger). The nano scale collagen can be produced with an average size of 200 nm as shown in the FIG. 2, or sizes or averages ranging from 1 nm to 900 nm, 10 nm to 800 nm, or from 100 nm to 500 nm. The scale of FIGS. 1 and 2 are similar, and as such show that the nano scale collagen of FIG. 2 is substantially smaller than the collagen of FIG. 1. The nano scale collagen of FIG. 2 has been studied with cell culture test for osteoblast growth, and the nano scale collagen shows about 30% improvement of cell growth in comparison with the micron scale collagen of FIG. 1. With the embrittling and attrition technique, large amounts of the nano scale collagen can be produced with relatively uniform size of about or less than 200 nm.

The process is also able to be scale up to manufacturing scale. Larger quantities, such as grams, 10s of grams, 100s of grams, kilograms, or larger can be prepared. The embrittling and reduction process allows for almost any amount of collagen to be reduced to nano scale particles.

The nano scale collagen particles can be included in compositions with a variety of materials. For example, the nano scale collagen of FIG. 2 can be prepared into a composition with a biocompatible material for use in therapies that need cell growth, proliferation, and penetration into the biocompatible material, such as a wound which needs primary and/or secondary healing.

In some instances, the collagen particles can be included with non-biodegradable materials (e.g., biostable polymers), which can be biocompatible and useful for various medical devices and drug delivery systems for external use or situations where biodegradability is not necessary such as in extractable medical devices that are removed from a body after use. Some examples of non-biodegradable polymers can include polyethylenes, polypropylenes, polyvinylchlorides, polystyrenes, and polycarbonates as well as others. Also, the collagen particles can be included with biodegradable materials, such as biodegradable polymers. Examples of some biodegradable polymers can include polyhydroxyalkanoates, polyhydroxybutyrate-valerate, polylactic acid, polylactates, polyglycolic acids, polyglycolides, polycaprolactones, polyvinyl alcohols, combinations thereof, and others. As such, the thin membrane can include a plurality of nano scale collagen particles incorporated into a biodegradable material. The nano scale collagen particles can be substantially uniformly distributed within the composition, or pockets or depots of the collagen particle can be formed. Gradients of collagen particles can also be useful.

For example, the composition can be formed into a thin membrane with a substantially homogeneous distribution of the nano scale particles. Such a membrane can include nano scale collagen particles having an average dimension of about 200 nm. Also, the thin membrane can have a thickness from about 10 microns to about 100 microns or larger. Examples can be from about 20 to 80 microns, about 30 to 70 microns, about 40 to 60 microns or about 50 microns.

The thin film can be prepared with nano scale collagen and biocompatible polymers and have a wide range of thickness and cross-sectional profiles and shapes. For example, the nano scale collagen can be combined with a biodegradable polymer such as polylactic-co-glycolic acid) (PLGA) to produce large area membranes or any size that is desired. The membrane optionally can be biodegradable which allows cell colonization and proliferation into the membrane. During the wound healing, the membrane disappears by itself and is absorbed into the body. In situations of secondary healing, such biodegradation can reduce or eliminate a need for a second surgery to remove of the membrane or bandage prepared therefrom. Such biodegradability avoids the presence of biologically incompatible foreign material in the human body that could pose rejection and inflammation. Thus, the thin membrane can have improved healing benefits.

A method for manufacturing a thin membrane can include mixing nano scale collagen particles with a biocompatible material, and forming a thin membrane to include the nano scale collagen particles with the biocompatible material. The process of forming the membrane can include various types of methods of membrane formation, such as spin-coating the biocompatible material and nano scale collagen particles onto a substrate. Other methods can be used to cast the composition into a thin membrane such as: casting and evaporating solvent; spray and dry; molding; deposition; lyophilization; compression; weaving; and other processes.

The manufacturing method can produce a composition, such as a thin membrane, that includes the nano scale collagen particles being substantially uniformly distributed within the article. Homogeneously mixing the biocompatible material and nano scale collagen particles can provide a homogeneous composition. For example, spin-coating a mixture of the biocompatible material and nano scale collagen particles onto a substrate can produce the homogeneous distribution in the thin film. The substrate can include a silicone rubber, ceramic, or metal material that can be easily removed from the thin membrane. In order to effect the spin-coating process, the biocompatible material can be provided in a solution and can be mixed with the nano scale collagen particles within the solution. The solution can be any organic solvent, such as dichloromethane, acetone, methyl acetate, ethyl acetate, chloroform, diethyl ether, tetrahydrofuran, dimethylformamide, acetonitrile, dimethyl sulfoxide, or others. The solution that is sprayed in the spin-coating process can be prepared to include the biocompatible material and nano scale collagen particles from about 1% to about 80% by weight of the solution, about 5% to about 60%, or about 10% to about 40%.

The thin membrane can be used for wound management and can be placed on or within a wound of a subject. The thin membrane with nano scale collagen particles can be useful for wound management because the collagen particles can be favorable for cell infiltration into the membrane and healing.

A wound dressing can include one or more nano scale collagen particles, and a biodegradable material having the one or more nano scale collagen particles, wherein the biodegradable material is configured as a wound dressing. The wound dressing can be resiliently flexible such that the dressing can flex and return to its shape. Also, the wound dressing can be configured as a bandage, gauze, film, gel, paste, solid, or combination thereof. The configuration of the dressing, such as a thin membrane, can absorb wound exudates, such as blood or other body fluid. Also, the dressing can be configured to debride a wound, and absorb wound particulates.

The wound dressing can be configured to promote clotting, and thereby can include a clot-forming API, such as tranexamic acid. Also, the dressing can be configured to inhibit infection by being sterile and/or including antimicrobial APIs.

The wound dressing can also be configured for cell migration and proliferation. As such, the wound dressing can have characteristics of the cell culture article or the tissue engineering scaffold as described. For example, the wound dressing can be porous, which can facilitate cell infiltration. Thus, the dressing can be configured to promote wound healing.

A method of wound healing can include introducing a wound dressing into a wound of a subject. The wound dressing can be configured with the biodegradable material having the nano scale collagen particles. The biodegradable material can be a biodegradable polymer as recited above. The wound dressing can include nano scale collagen particles have an average dimension of about 1 nm to about 1 micron. The wound dressing can have a thickness from about 1 to about 100 microns.

The thin membrane can also include active pharmaceutical ingredients (API) that are favorable for wound management, which can include cellular and tissue development promoting APIs. Examples can include antibiotics, analgesics, NSAIDs, anticeptics, antipyretics, anti-inflammatories, anticoagulants, antiplatelets, hemostatics, anaesthetics, opioids, anti-allergens, emollients, anti-purities, antifungals, scabicides, vitamin A, and many others. Also, the membrane can be configured for drug delivery and the API can be any type of biologically active agent for any use or indication. Specific examples of APIs that can be included are antimicrobial agents and/or agents configured to promote wound healing.

In one embodiment, the composition having the biocompatible material and nano scale collagen particles can be configured as an article for cell culture. The cell culture article can be conditioned to include a cell culture medium associated with the nano scale collagen particles. For example, the biodegradable material and nano scale collagen particles can be configured into a tissue scaffold, a cell culture article, a cell culture insert, or other. The cell culture insert can have a shape configured to be received into a cell culture chamber, such as a cell culture chamber in a multi-chamber cell culture plate. The composition can be porous to facilitate cell penetration, migration, and proliferation. Otherwise the composition can be non-porous to inhibit cell penetration, migration, and proliferation depending on the use.

In one embodiment, the composition having the biocompatible material and nano scale collagen particles can be configured as a cell culture insert. Such a cell culture can be configured to fit into a cell culture chamber. The cell culture chamber can be a standalone chamber or one of many chambers in a multi-chamber plate (e.g., 96-well plate). The cell culture insert can be configured for cell migration and proliferation so that cells can migrate and proliferate through the cell culture insert. For example, the insert can be porous. Alternatively, the insert can be configured to receive cells thereon such that the cells do not penetrate or migrate into the insert which is not porous and made of a biostable material (e.g., biostable polymer). The biostable polymer can be selected from polystyrenes, polyethylenes, polypropylenes, polycarbonates, polyolefins, or combinations thereof. The insert can be substantially rigid with limited flexibility, which can be represented by standard cell culture articles.

In one embodiment, the cell culture insert can be biodegradable. That is, the insert can degrade in the presence of cell culture media and/or cells by being formed of a biodegradable material, such as a biodegradable polymer. The biodegradable polymer can include one or more monomers of lactic acid and/or glycolic acid or salt thereof. Also, the biodegradable polymer can include starches, celluloses, polysaccharides, polyhydroxyalkonoates, polyesters, polyalkylene esters, polylactic acids, polyamide esters, polyvinyl esters, polyvinylalcohols, polyanhydrides, combinations thereof, copolymers thereof, or monomers thereof.

Also, one or more cells can be associated with the nano scale collagen particles. In one example, the one or more cells can include an epithelium cell. Examples of cell types can further include prokaryotic cells, eukaryotic cells, bacteria, archaea, epidermal, epidermal keratinocyte, epidermal basal cell, keratinocytes, basal cell, medullary hair shaft cell, cortical hair shaft cell, cuticular hair shaft cell, cuticular hair root sheath cell, hair matrix cell, wet stratified barrier epithelial cells, gland cells, hormone secreting cells, metabolism cells, storage cells, barrier function cells, ciliated cells, extracellular matrix secretion cells, contractile cells, blood cells, immune system cells, nervous system cells, pigment cells, germ cells, nurse cells, interstitial cells, or others as well as combinations thereof.

The composition having the biocompatible material and the nano scale collagen can be used in cell culture methods. Cell cultures can be grown with the composition by applying cells thereto, and then maintaining the cells with an appropriate medium. The configuration of the composition can be as a cell culture insert or other cell culture article. For example, a cell culture method can include introducing a cell culture insert into a cell culture chamber, and culturing one or more cells in the cell culture chamber such that the one or more cells grow and/or proliferate. The cell culture article can allow the cells to migrate and/or proliferate on or within the cell culture insert. The cell culture method can include combining the one or more cells with the cell culture insert before, during, or after being introduced into the cell culture chamber. The cell culture method can also include introducing the one or more cells and a cell culture medium into the cell culture chamber.

The composition having the biocompatible material and the nano scale collagen can be configured as a tissue implant article. The tissue implant article can be a tissue engineering scaffold with or without cells. The tissue implant article can include a biodegradable scaffold having one or more nano scale collagen particles, and can include one or more cells on or in the biodegradable scaffold. Optionally, the tissue implant article can include a cell culture media in contact with the one or more cells. The one or more cells of the tissue implant can be dead or alive, and can be disperse or form a tissue.

A method of implanting cells in a subject can include obtaining a tissue implant article as described, and implanting the implant article into a subject. The implant article can be implanted with or without media in contact with the cells, and in some instances media can be removed or added before implantation.

EXAMPLES

The process to produce nano scale collagen includes embrittling then size reduction. Firstly, commercially available micron scale collagen powder is obtained and immersed in liquid nitrogen in direct contact for 30 minutes. Next, the cryo-collagen is placed under vacuum for 48 hours to sublime water from the collagen. The freeze dried collagen is subjected to high energy impaction milling/attrition to obtain very fine nano scale collagen powders/particles. The high energy milling process includes 500 RPM rotational speed for 20-30 hours. The milling ball used is mixture between 10 mm, 3 mm and 2 mm diameter with the weight ratio of 1:1:1 for each milling ball size. For each milling, the amount of freeze dried collagen to start is maximum 1:5 weight ratio with milling balls in a 120 ml volume milling vessel.

This process is able to produce nano scale collagen with the average size of 200 nm (FIG. 2). The nano scale collagen has been studied in cell culture tests with osteoblasts, and shows about 30% improvement of cell growth in comparison with the micron size collagen as shown in FIG. 3. FIG. 3 shows that the nano scale collagen having improved cell growth compared to micron scale and acidified nano scale collagen.

Figure 4:
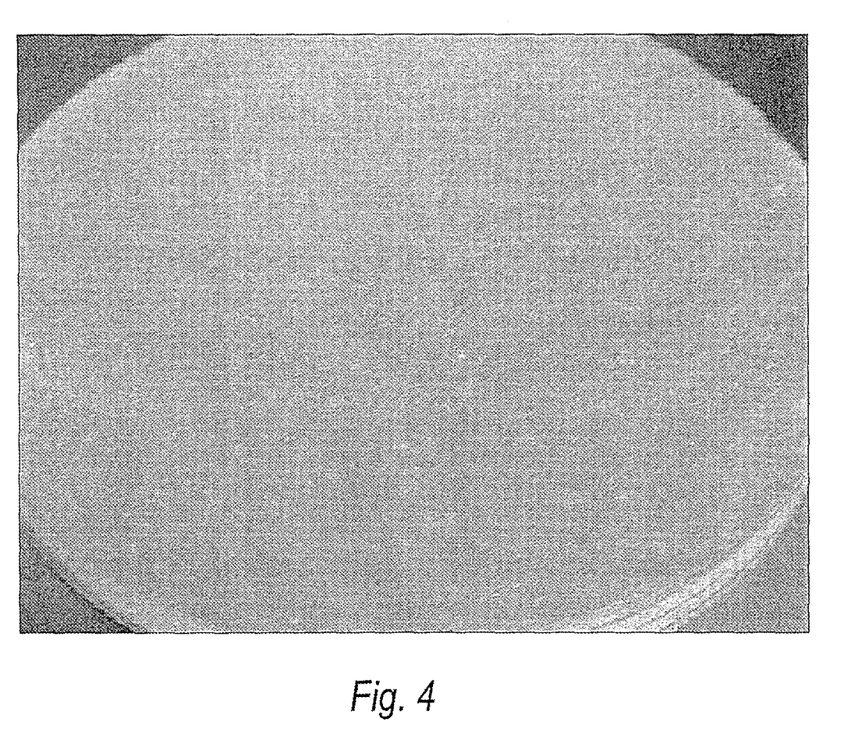
FIG. 4 is an example of an image of a composite membrane of PLGA having nano scale collagen which was prepared by spin coating.
Figure 5:
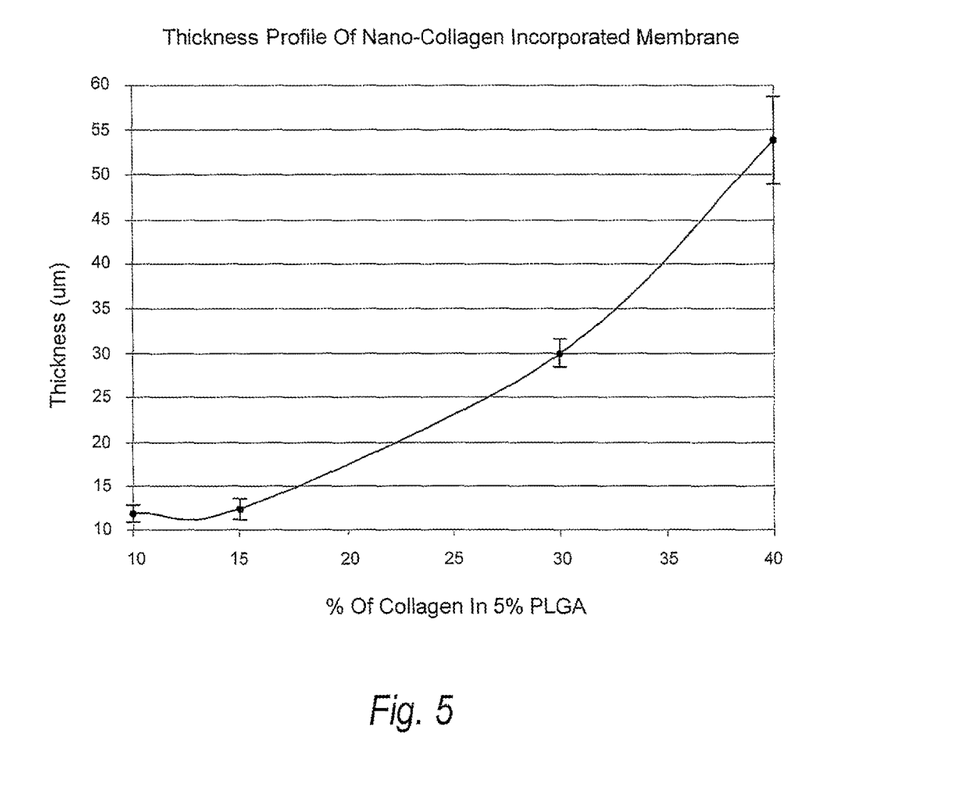
FIG. 5 is an example of a graph that a composite membrane of PLGA having nano scale collagen thickness profile against the nano scale collagen content

The membrane can be prepared by mixing the nano scale collagen and biodegradable material and then using any process that can prepare a flat membrane. Briefly, the nano scale collagen powder is mixed with a 5 wt % PLGA polymer solution dissolved with dichloromethane solvent. For example, a polymer mixture of 10 wt %, 15 wt %, 30 wt %, and 40 wt % of nano scale collagen with respect to the PLGA polymer solution were prepared. The polymer mixture is spin coated on a special substrate made of PDMS/Silicone rubber at 4000 RPM. FIG. 4 shows a PLGA-nano scale collagen thin membrane. The profile of the membrane thickness against the nano collagen content is shown in FIG. 5. The thickness of the membrane is shown to be between about 10-50 microns, which is suitable for application in wound healing of epithelial cells. However, larger thickness membranes can be prepared.

Manufacturing a thin membrane with micron scale collagen was not successful. Due to the physical-chemical limitations of micron scale collagen, the PLGA membrane solution become very viscous and impossible to process into a thin membrane even at 0.5% concentration of micron scale collagen.

Figure 6:
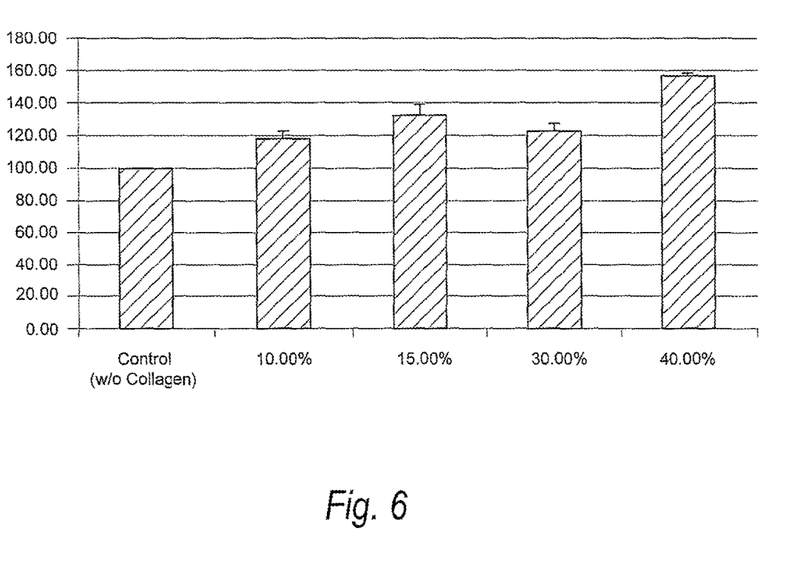
FIG. 6 is an example of a graph illustrating acute (24 hr) effect of collagen membrane concentrations on H2C9 proliferation.
Figure 7:
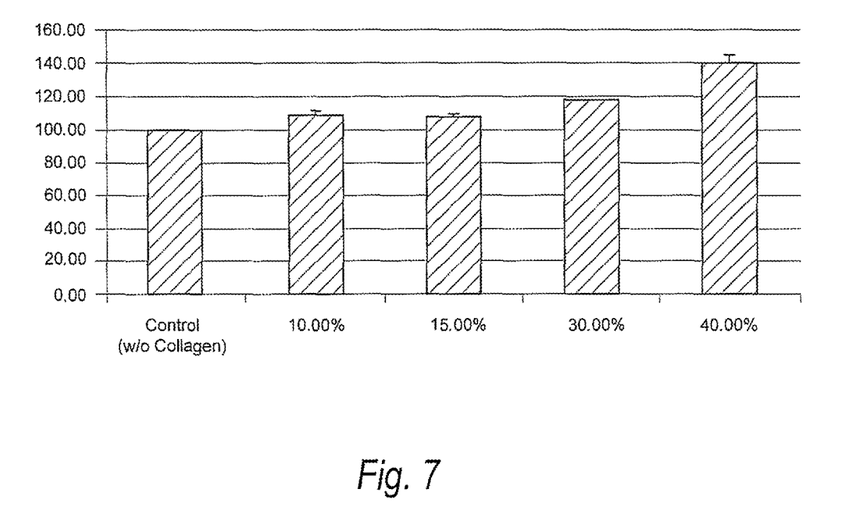
FIG. 7 is an example of a graph illustrating sub-acute (48 hr) effect of collagen membrane concentrations on H2C9 proliferation.

The nano scale collagen thin membranes were also tested on various cells. One cell that is biomedically interesting is the H2C9 cell line (cardiac cell line), which is an epithelium cell type similar to blood vessels and most of other epithelium cells. The cells are incubated with the presence of the membranes and after 24 and 48 hours of incubation period, the number of cells proliferation were counted, and which show a significant amount of improvement in cell proliferation compared with the controlled sample (e.g., a blank PLGA membrane without any nano scale collagen particles). Graphs showing the improvement in the cell proliferation after 24 and 48 hours are shown in FIGS. 6 and 7.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along With the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A method for manufacturing a thin membrane, the method comprising:
   embrittling a powder composition of micron-sized collagen particles by contacting the collagen particles or a vessel containing the collagen particles with a cryogenic fluid and drying the collagen particles under vacuum so as to remove water from the collagen particles to produce an embrittled collagen powder;
   reducing a size of the collagen particles of the embrittled collagen powder obtained by embrittling to produce collagen powder having a nano scale dimension by ball milling the embrittled collagen powder;
   mixing the nano scale collagen particles with a biocompatible material; and
   spin-coating the biocompatible material and nano scale collagen particles onto a substrate so as to form a thin membrane having the nano scale collagen particles distributed in the biocompatible material, wherein the nano scale collagen particles exhibit an increased osteoblast growth as compared to acidified collagen particles.

2. The method of claim 1, wherein the collagen particles have a dimension greater than about 1 micron prior to embrittling and the nano scale collagen particles have an average dimension of about 1 nm to 1 micron.

3. The method of claim 1, wherein the embrittling includes:
   placing the composition of collagen particles into a vessel;
   contacting the vessel with a cryogenic fluid; and
   placing the vessel under vacuum to reduce pressure inside the vessel so as to sublime water from the collagen particles.

4. The method of claim 1, wherein ball milling the embrittled collagen powder includes milling the collagen particles with one or more milling balls.

5. The method of claim 1, wherein the substrate includes a silicone rubber.

6. The method of claim 1, wherein the biocompatible material is provided in a solution from about 1% to about 40% by weight of the solution before spin-coating.

7. The method of claim 1, wherein the thin membrane has a thickness from about 1 micron to about 100 microns.

8. The method of claim 1, wherein the biocompatible material includes a biodegradable polymer.

9. The method of claim 8, wherein the biodegradable polymer is selected from the group consisting of polyhydroxyalkonoates, polyesters, polyalkylene esters, polylactic acids, polyglycolic acids, polyamide esters, polyvinyl esters, polyvinylalcohols, polyanhydrides, combinations thereof, copolymers thereof, and monomers thereof.

10. The method of claim 1, wherein the nano scale collagen particles are substantially uniformly distributed within the biocompatible material.

11. The method of claim 1, further comprising mixing an active pharmaceutical ingredient with the biocompatible material and collagen particles.

12. The method of claim 1, further comprising configuring the thin membrane into one of the following:
   a wound dressing;
   a tissue scaffold; or
   a cell culture insert having a shape configured to be received into a cell culture chamber.

13. The method of claim 1, wherein the acidified collagen particles comprise acidified micron scale collagen particles.

14. The method of claim 1, wherein the nano scale collagen particles exhibit the osteoblast growth that is about 30% greater than that exhibited by acidified micron scale collagen particles.

15. The method of claim 1, wherein the acidified collagen particles comprise acidified nano scale collagen particles.

16. The method of claim 1, wherein the mixing the nano scale collagen particles with a biocompatible material results in uniformly distributed nano scale collagen particles within the biocompatible material.

17. The method of claim 1, wherein the mixing the nano scale collagen particles with a biocompatible material results in a formation of pockets of nano scale collagen particles distributed within the biocompatible material.

18. The method of claim 1, wherein the mixing the nano scale collagen particles with a biocompatible material results in a gradient.

19. The method of claim 1, wherein the thin membrane has a thickness from about 10 microns to about 50 microns.

20. A thin membrane comprising nano scale collagen particles within a biocompatible material, the thin membrane being formed according to a method comprising:
   embrittling a powder composition of micron-sized collagen particles by contacting the collagen particles or a vessel containing the collagen particles with a cryogenic fluid and drying the collagen particles under vacuum so as to remove water from the collagen particles to produce an embrittled collagen powder;

reducing a size of the collagen particles of the embrittled collagen powder obtained by embrittling to produce collagen powder having a nano scale dimension by ball milling the embrittled collagen powder;

mixing the nano scale collagen particles with the biocompatible material; and spin-coating the biocompatible material and nano scale collagen particles onto a substrate so as to form a thin membrane having the nano scale collagen particles distributed in the biocompatible material, wherein the nano scale collagen particles exhibit an increased osteoblast growth as compared to acidified collagen particles.

21. The thin membrane of claim 20, wherein the nano scale collagen particles exhibit increased osteoblast growth as compared to micron scale collagen.

22. The thin membrane of claim 20, wherein the nano scale collagen particles exhibit osteoblast growth that is about 30% greater than that exhibited by micron scale collagen.

23. The thin membrane of claim 20, wherein the nano scale collagen particles are substantially uniformly dispersed within the biocompatible material.

24. The thin membrane of claim 20, wherein the nano scale collagen particles are distributed in the biocompatible material as pockets of the nano scale collagen particles.

25. The thin membrane of claim 20, wherein the nano scale collagen particles are distributed within the biocompatible material so as to have a gradient.

26. The thin membrane of claim 20, wherein the thin membrane has a thickness from about 10 microns to about 50 microns.

* * * * *